United States Patent [19]
Hench et al.

[11] Patent Number: 5,981,412
[45] Date of Patent: Nov. 9, 1999

[54] BIOACTIVE CERAMICS AND METHOD OF PREPARING BIOACTIVE CERAMICS

[75] Inventors: Larry L. Hench, London, United Kingdom; Guy La Torre, Gainesville, Fla.; Oscar P. Filho; Edgar Zanotto, both of Sao Carlos, Brazil

[73] Assignee: University of Florida Research Foundation, Gainesville, Fla.

[21] Appl. No.: 08/850,318

[22] Filed: May 1, 1997

Related U.S. Application Data

[60] Provisional application No. 60/017,173, May 1, 1996.

[51] Int. Cl.$^6$ ................ C03C 10/04; A61F 2/28
[52] U.S. Cl. ................ 501/5; 501/63; 501/72; 106/35; 623/16; 623/66; 523/114; 523/115
[58] Field of Search ............ 501/5, 72, 63; 106/35; 623/16, 66; 523/114, 115

[56] References Cited

U.S. PATENT DOCUMENTS

| | | |
|---|---|---|
| 3,981,736 | 9/1976 | Broemer et al. . |
| 4,103,002 | 7/1978 | Hench et al. . |
| 4,605,415 | 8/1986 | Richez . |
| 4,708,652 | 11/1987 | Fujiu et al. . |
| 5,074,916 | 12/1991 | Hench et al. ................ 501/72 |
| 5,120,340 | 6/1992 | Ducheyne et al. . |
| 5,171,326 | 12/1992 | Ducheyne et al. . |
| 5,204,106 | 4/1993 | Schepers et al. . |
| 5,204,382 | 4/1993 | Wallace et al. . |
| 5,352,715 | 10/1994 | Wallace et al. . |
| 5,429,996 | 7/1995 | Kaneko . |
| 5,645,934 | 7/1997 | Marcolongo et al. . |
| 5,648,301 | 7/1997 | Ducheyne et al. . |
| 5,681,872 | 10/1997 | Erbe ................ 106/35 |
| 5,735,942 | 4/1998 | Litkowski et al. ................ 501/72 |
| 5,762,950 | 6/1998 | Yli-Urpo et al. ................ 501/72 |

FOREIGN PATENT DOCUMENTS

WO93/17976  9/1993  WIPO .

*Primary Examiner*—Karl Group
*Attorney, Agent, or Firm*—Burns, Doane, Swecker & Mathis, L.L.P.

[57] ABSTRACT

A bioactive ceramic composition including 47 to 51% $SiO_2$, 23 to 25% CaO, 23 to 25% $Na_2O$ and 0 to 6% $P_2O_5$, the bioactive ceramic having a bioacitivity level such that the composition forms at least a thin layer of HCA within about 30 hours of implantation into a patient. The bioactive ceramic composition having a crystallinity of 34 to 60 volume percent and a crystalline phase of $1Na_2O.2CaO.3SiO_2$.

19 Claims, 20 Drawing Sheets

5,981,412

BIOACTIVE CERAMICS AND METHOD OF PREPARING BIOACTIVE CERAMICS

RELATED APPLICATION

This application is a continuation-in-part application of U.S. provisional application No. 60/017,173, filed May 1, 1996, the subject matter is hereby incorporated by reference.

This invention was made with government support under contract number F49620-92-J-O351, awarded by a grant from the U.S. Air Force. The government has certain rights in the invention.

FIELD OF THE INVENTION

The present invention relates to novel bioactive ceramic compositions as well as to a process for preparing such ceramic compositions. The present invention also relates to various orthopedic methods of treatment including the use of such bioactive ceramic compositions in load bearing prosthetic devices. The present invention also relates to a method for making such bioactive ceramics.

BACKGROUND OF THE INVENTION

A common characteristic of all bioactive implants is formation of a hydroxy-carbonate apatite (HCA) layer on their surface when implanted. The substance of human bone is essentially hydroxyapitite ($Ca_5[(OH)-(PO_4)_3]$) that is permeated with collagen. The regeneration of bone substances proceeds from mineral hydroxyapatite. It is believed that this substance acts as a point of attachment for bone substance. Starting from hydroxyapatite nuclei, a substantially complete bone is thus regenerated and built up. A bioactive material undergoes chemical reactions at the interface between tissues and the implant material. The surface reactions lead to bonding of tissues at the interface. The level of bioactivity in bioactive ceramics is dependent on composition and structure. Similarly, the mechanical properties of glass-ceramics, among others variables, depend on volume fraction, grain size, crystal phase and shape of crystals. Accordingly, the composition and method of manufacture of bioactive ceramics can have great effect on the resultant properties of the ceramic.

The processing of glass-ceramic materials has classically been viewed as a two-stage event consisting of nucleation and growth stages. The nucleation kinetics for glass-ceramic systems are described by nucleation rate curves. The most common method for generation of nucleation rate curves is the two-stage method. The first step is the production of a matrix of nucleated samples by heat treating the parent glass at varying heat treatment temperatures and heat treatment times. This matrix of samples is given a second heat treatment of sufficient time and temperature that the nuclei generated in the first step are grown to a microscopically observable size.

The growth kinetics are described by growth rate curves, which are also determined with the two-stage method. During in the first step all samples are nucleated with the same thermal treatment. In the second step, the nuclei are grown with varying heat treatment times and heat treatment temperatures. By optical microscopy measurements, the crystal size evolution for a specific temperature is determined as function of heat treatment times and a growth rate is calculated.

Previous bioactive ceramics have proven unsatisfactory because they fail to combine both the advantages of superior physical strength and a high level of bioactivity. For example, one disadvantage of known glass ceramics is their relatively low tendency to form nuclei. Furthermore, the number of nuclei formed per unit of volume is very difficult to control technologically since it is dependent on numerous factors. See U.S. Pat. No. 3,981,736 (Column 2, lines 58–68).

WO 93/17976 discloses bioactive glasses or glass ceramics, in granular form, as bone substitutes. They are described as useful for filling e.g. craniofacial bone defects, sinus lift, alveolar augmentation and bone cysts. The glasses disclosed have the following composition:

| | |
|---|---|
| $SiO_2$ | 53.0–62.0% |
| $Na_2O$ | 15.0–30% |
| CaO | 10.0–25.0% |
| $P_2O_5$ | 0.0–8.0% |
| $B_2O_3$ | 0.0–3.0% |
| $Al_2O_3$ | 0.0–1.5% |

The process disclosed for making the ceramic material includes mixing the raw materials and heating them at about 1350° C. for several hours. After this the melt is poured on a graphite plate and annealed at about the glass transition temperature of the glass for one to several hours. The glass is then crushed and ceramics are produced by heating the base glass to about 650–1000° C. for several hours. These compositions have the disadvantage of low bioactivity.

Accordingly, it is an object of the present invention to provide a bioactive ceramic with both high bioactivity and controlled mechanical properties similar to natural bone.

It is further an object of the present invention to provide a method for preparing such superior bioactive ceramics.

SUMMARY OF THE INVENTION

The present invention is directed to a bioactive ceramic composition comprising 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient. The present invention is also directed to a method of preparing bioactive ceramic glass compositions as well as various methods of orthopedic treatment.

DETAILED DESCRIPTION OF THE INVENTION

Figure 1:
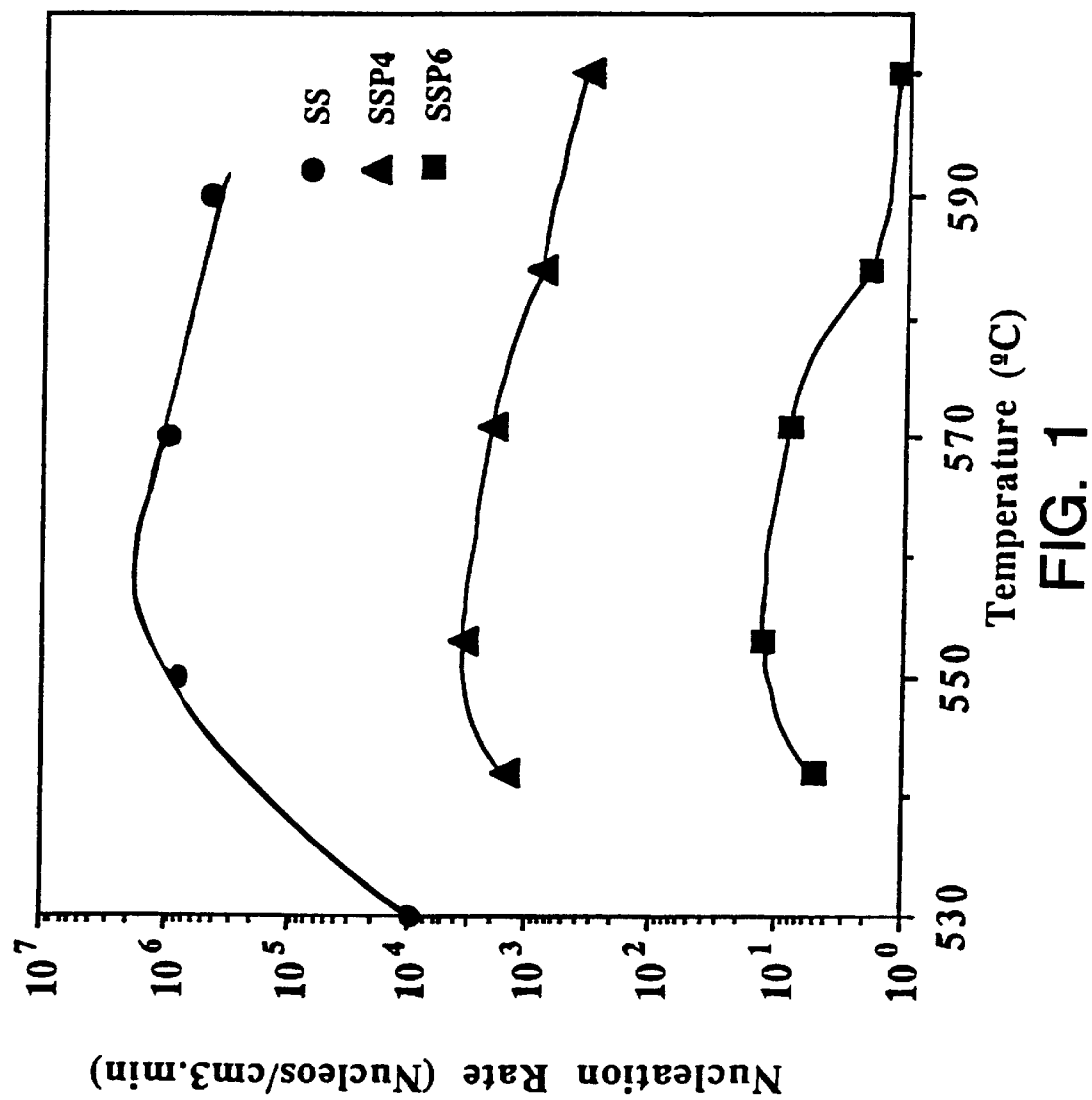
FIG. 1 shows the nucleation rates for the SS, SSP4 and SSP6 compositions as a function of temperature.

Applicants have unexpectedly discovered that bioactive ceramic glasses having a specific range of silica content provide for both superior physical and mechanical properties. If silica content of the ceramic is too low, the ceramic will have a poor three dimensional structure and therefore poor mechanical properties. If the silica content is too high, bioactivity is lost during the nucleation and crystallization necessary to form the ceramic. For example, compositions in accordance with the present invention are capable of forming an HCA layer in vitro in a matter of hours whereas previous compositions were not able to form an HCA layer for period of several days. If the HCA layer is not formed quickly, there is no adequate bone bonding.

Applicants have also discovered that within this compositional range of parent glasses (compositional ranges relating to the ceramic are always expressed in terms of the parent glass unless otherwise indicated), there is the ability to tailor the mechanical properties by altering the nucleation and provide crystallization schedules for the various compositions of glass. This results in an ability to control mechanical properties and more closely match the mechanical properties to those of natural bone tissues. By better matching the mechanical properties of the implant material and the surrounding in vivo tissues, one can avoid the problems of stress shielding. Stress shielding prevents the bone from being properly loaded. The clinical problem arises because bone must be loaded in tension to remain healthy. Stress shielding weakens bone in the region where the applied load is lowest or in compression. Bone that is unloaded or loaded in compression will undergo osteoclast proliferation that leads to bone resorption. Clinical success of an implant material requires the simultaneous achievement of fast bonding at the interface as well as a functional matching of mechanical properties. The technology presented here has the ability to generate a range of mechanical properties similar to natural bone by fine control of nucleation and crystallization.

Applicants have also discovered that within this compositional range of parent glasses, there is the ability to nucleate and crystallize the glass in very short time periods as compared to other glass ceramic processes. For example, many of the compositions in accordance with the present invention can be produced in a matter of a 24 hour period as compared to several days or weeks for other processes. This unexpectedly short manufacturing time is an economic advantage when compared to other glass ceramics. Compositions in accordance with the present invention are also useful in many applications including the regeneration of bone, spacers for spinal fusion, replacement of jaw bone and other load bearing bone. Accordingly, the present invention is also directed to various methods of treatment.

Compositions in accordance with the present invention may also be combined with composite materials such as prosthetic devices and can be used as autogenous bone chips. Composite materials can be formed by combination of ceramic compositions in accordance with the present invention and polysulfones, polyethylenes, polycarbonates, polylactic acids, polyglycolic acids, absorbable biopolymers, and urethanes. The bioactive ceramic can be added before or after polymerization in amounts preferably between 10 and 50% of the final composition by weight.

The following non-limiting examples are included to further illustrate some embodiments of the present invention.

EXAMPLES

Bioactive glass ceramics in accordance with the present invention were made having the following compositions:

I, Glass Compositions Prepared

The glasses used in the following experiments were made with high purity materials such as 5 microns silica, calcium carbonate, sodium carbonate and sodium phosphate. The glass compositions are given in table 1, as well the sample codes.

TABLE 1

Composition of SS glasses studied

| Code | COMPONENT (Weight %) | | | |
|------|------|------|------|------|
|      | $SiO_2$ | CaO | $Na_2O$ | $P_2O_5$ |
| SS   | 50.6 | 24.7 | 24.7 | 0.0 |
| SSP2 | 49.4 | 24.3 | 24.3 | 2.0 |
| SSP4 | 48.4 | 23.8 | 23.8 | 4.0 |
| SSP6 | 47.6 | 23.2 | 23.2 | 6.0 |

All batches were calculated to produce 140 grams of glass. The batch was mixed thoroughly for 3 hours on a ball mill.

The glasses were prepared by charging a platinum alloy crucible several times over a period of thirty minutes until the 140 gram glass batch was melted. Carbonate decomposition assured thorough mixing of each batch. Melting was carried out in a high temperature furnace with a digital thermal controller. The glass batches were melted over a range of temperatures between 1300 and 1360° C. All glass batches were homogenized for 5 to 7 hours to assure uniform composition. To enhance homogeneity, each forty minutes the crucible was taken from the furnace and shaken thoroughly until the glass become highly viscous. It was then reheated to the homogeneity temperature.

The glasses used for nucleation, crystallization and bioactivity studies were poured into graphite molds to form 8 mm×30 mm cylinders. The samples used in mechanical property studies were cast into a split graphite mold with a rectangular shape, 34 mm long and 5.5 mm thickness. After each sample was poured, the crucible was returned to the furnace and allowed to reach the melting temperature before the next sample was poured.

Each specimen was placed in an annealing furnace immediately after casting and allowed to soak at 450° C. for at least 7 hours. After annealing the cylinders were cut into disks of about 3 mm thickness. These disks were used to determine the nucleation and growth rates and the bioactivity of the glasses and glass-ceramics.

II. Nucleation and Crystallization

The processing of glass-ceramic materials has classically been viewed as a two-stage event consisting of nucleation and growth stages.

(A) Nucleation

The nucleation kinetics for glass-ceramic systems are described by nucleation rate curves. The most common method for generation of nucleation rate curves is the two-stage method. The first step is the production of a matrix of nucleated samples by heat treating at varying heat treatment temperatures and heat treatment times. This matrix of samples is given a second heat treatment of sufficient time and temperature that the nuclei generated in the first step are grown to a microscopically observable size.

Samples are then cut cross sectionally and polished. Polishing is done m two steps, first with SiC polishing paper of 320, 600 and 1200 grit, and a second final polish with $CeO_2$ (1 $\mu$m). To reveal the crystals, the polished surface is etched by HF (0.05%) solution for about 8 seconds.

Standard stereological measurements are then made on each sample. The volume nucleation rate is calculated from the number of nuclei per unit area, the average of the reciprocal diameter and crystal shape factor (eq. 1). The volume nucleation rate as function of temperature is determined using the following equation.

$$N_v = N/A \cdot \psi \cdot [\Sigma(1/d)]/n, \text{ and } \psi=1 \text{ to cubic and } 2/\pi \text{ to spherical} \quad (1)$$

where $N_v$ is volume nucleation rate, N number of crystals, A area, $\Psi$ shape factor, d diameter or diagonal of crystals.

FIG. 1 shows the nucleation rates for the SS, SSP4 and SSP6 compositions as a function of temperature. The $P_2O_5$ content has a dramatic effect on the nucleation rate. Only 4% $P_2O_5$ is enough to decrease the nucleation rate by $10^3$ times. It is more pronounced when the amount of $P_2O_5$ is at 6% and the nucleation rate drops by $10^6$ times. However, maximum nucleation rate temperatures did not show significant changes with increase $P_2O_5$ content; i.e., 560, 555 and 555° C. for SS, SSP4 and SSP6 compositions.

B. Growth Rate

The growth kinetics are described by growth rate curves, which are also determined with the two-stage method. During in the first step all samples are nucleated with the same thermal treatment. In the second step the nuclei are grown with varying heat treatment times and heat treatment temperatures. By optical microscopy measurements, the crystal size evolution for a specific temperature is determined as function of heat treatment times and a growth rate is calculated. Growth rates curves are developed as a function of the growth temperature (FIG. 2).

Figure 2:
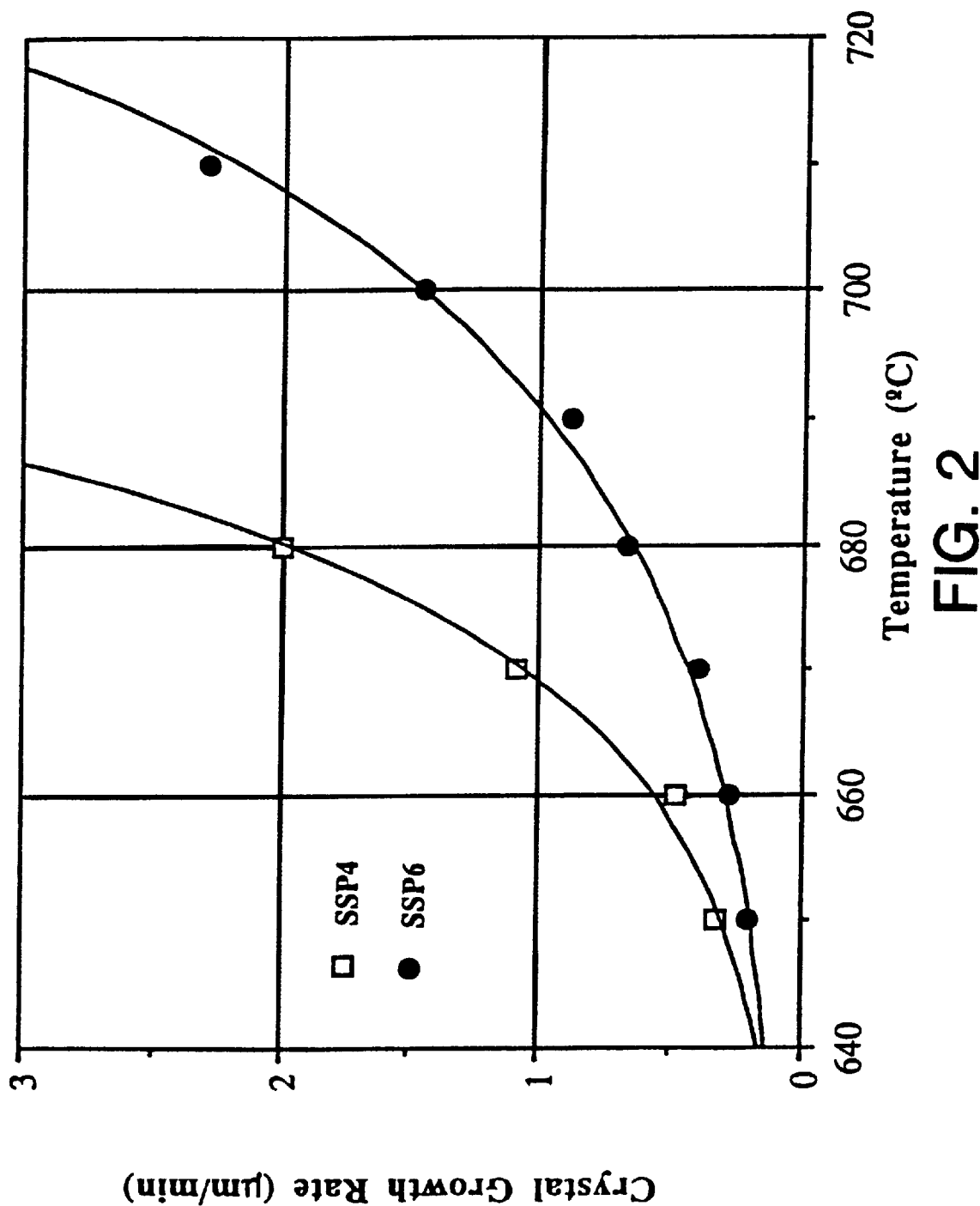
FIG. 2 shows the crystal growth rate for SSP4 and SSP6 compositions.
Figure 3A:
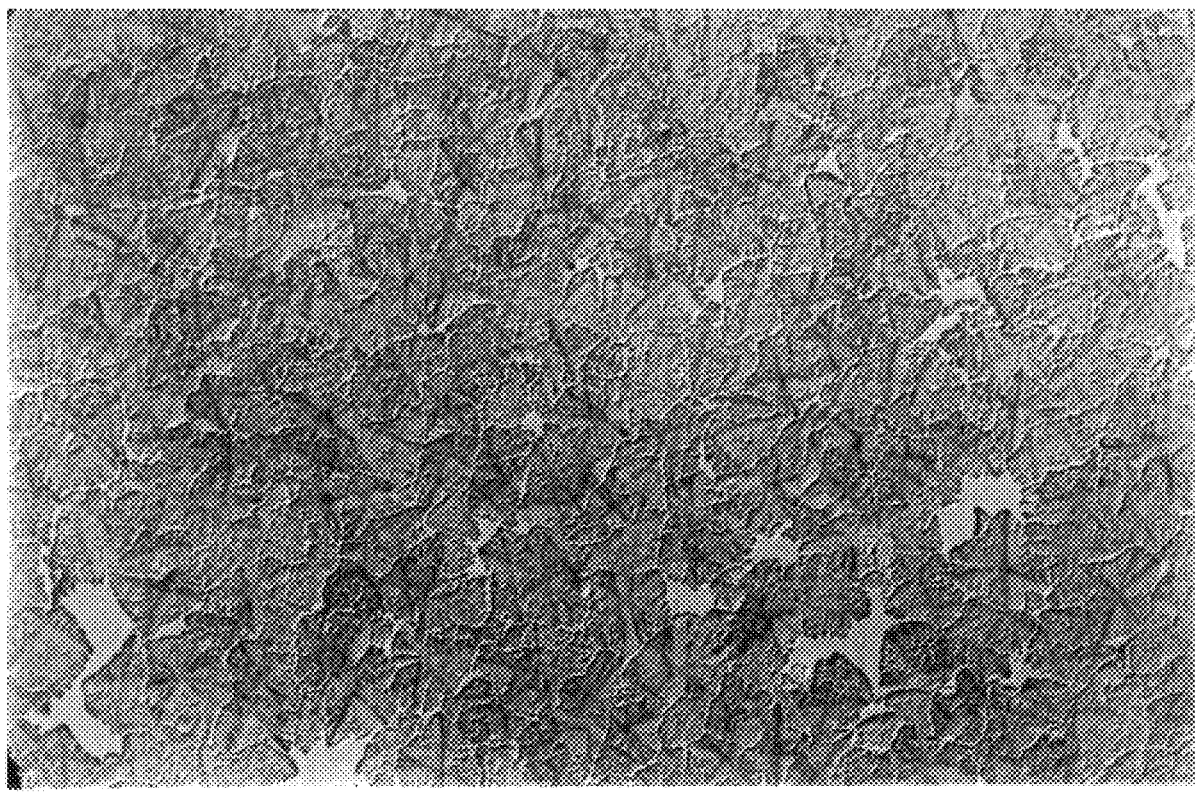
FIG. 3 presents the optical microstructures of glass-ceramics for several volume percentages of crystallization (8, 36, 60, 87 and 100%) for the SSP6 composition.
Figure 3B:
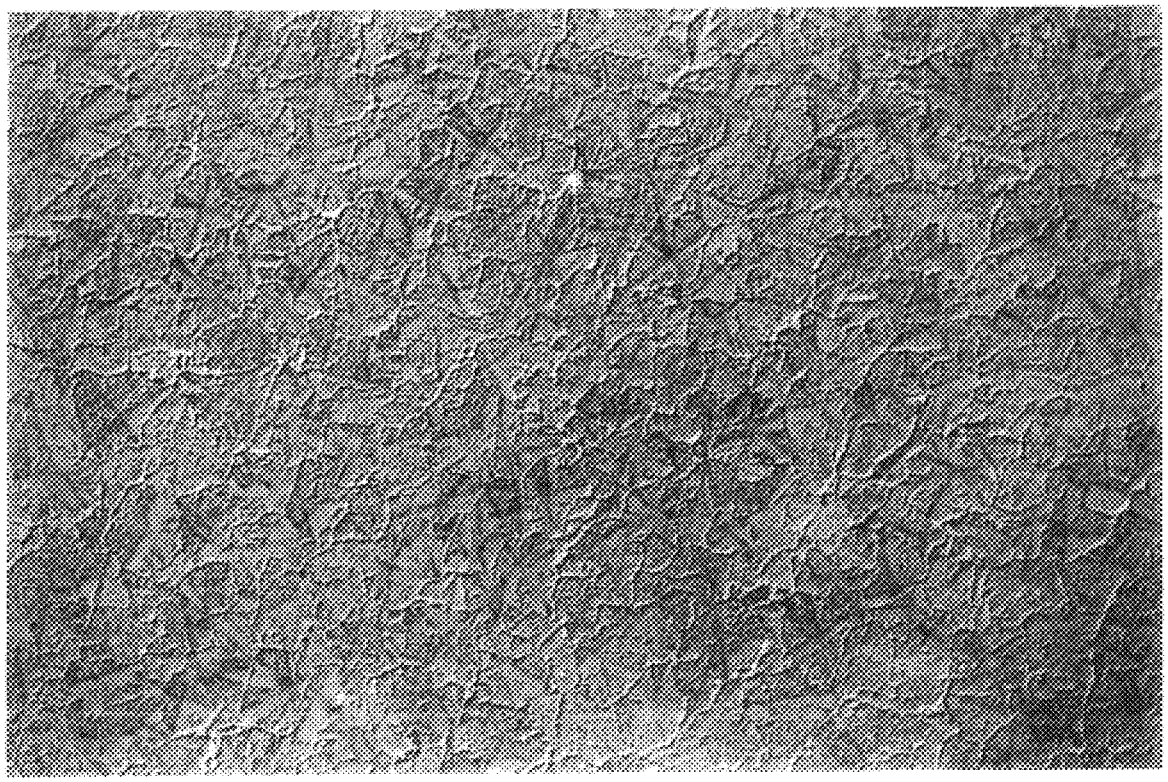
Figure 3C:
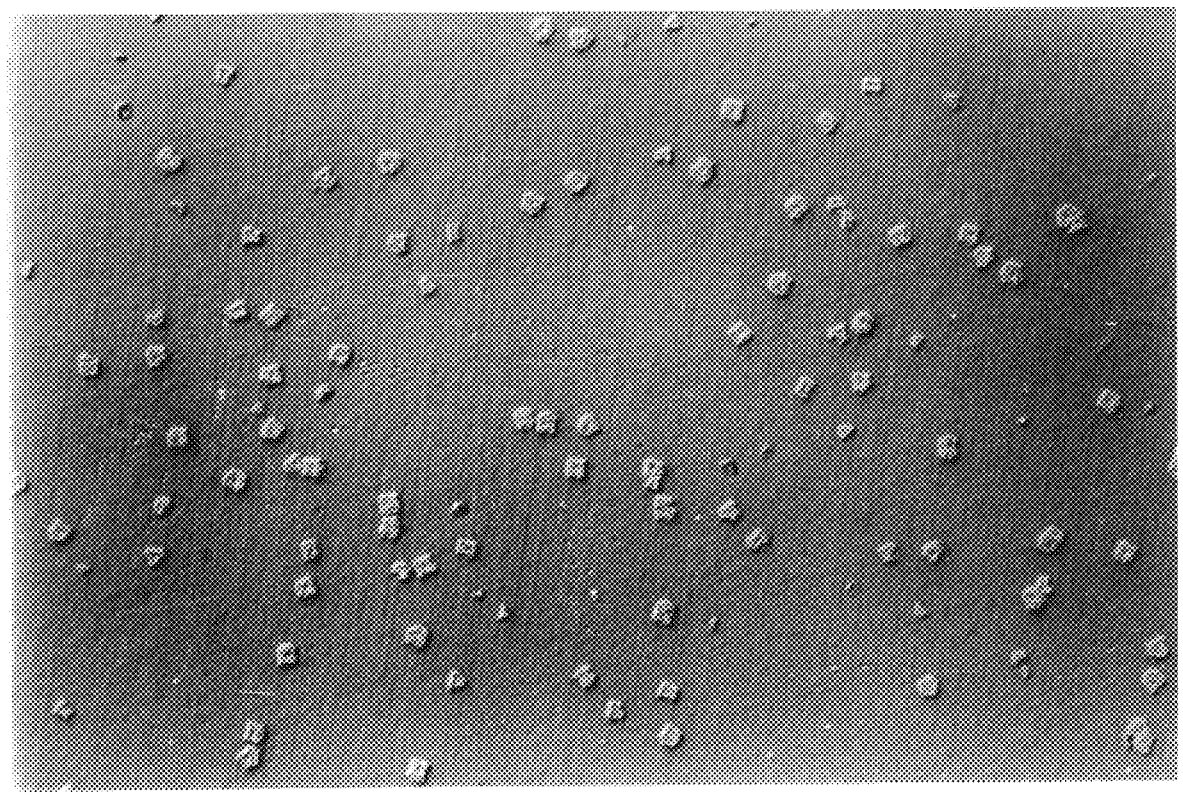
Figure 3D:
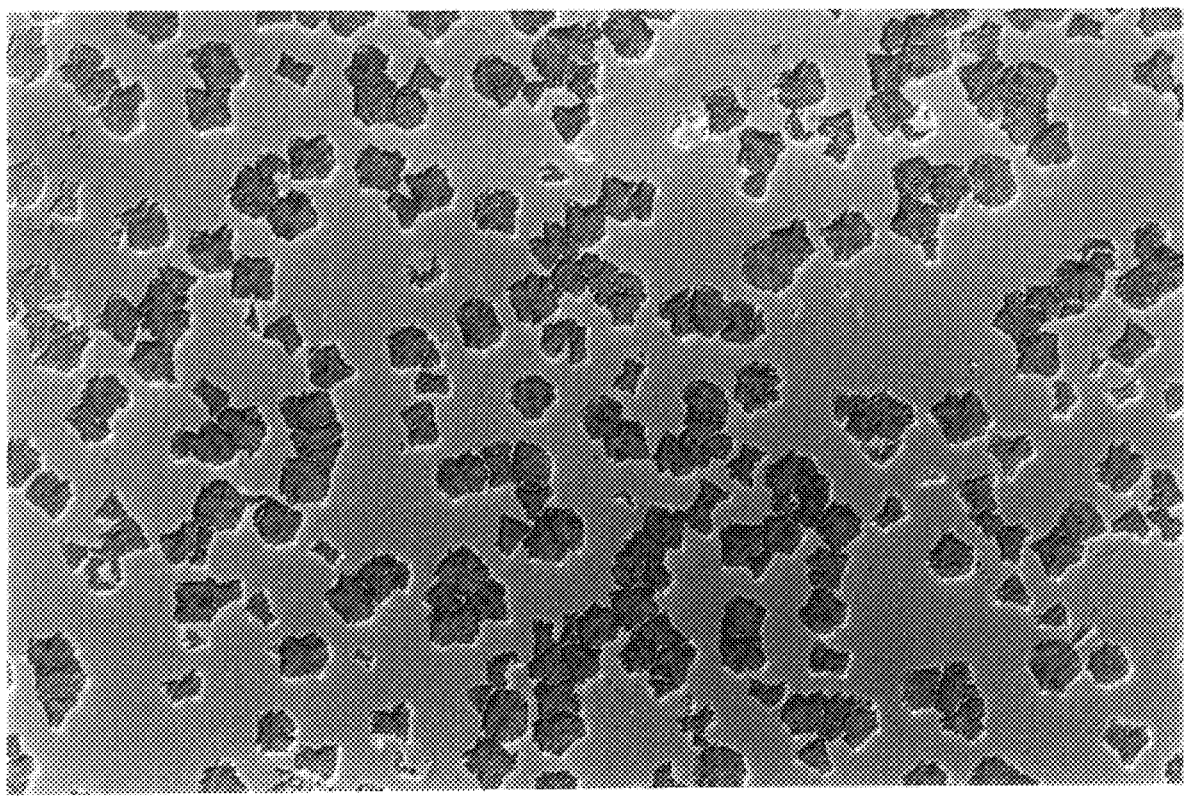
Figure 3E:
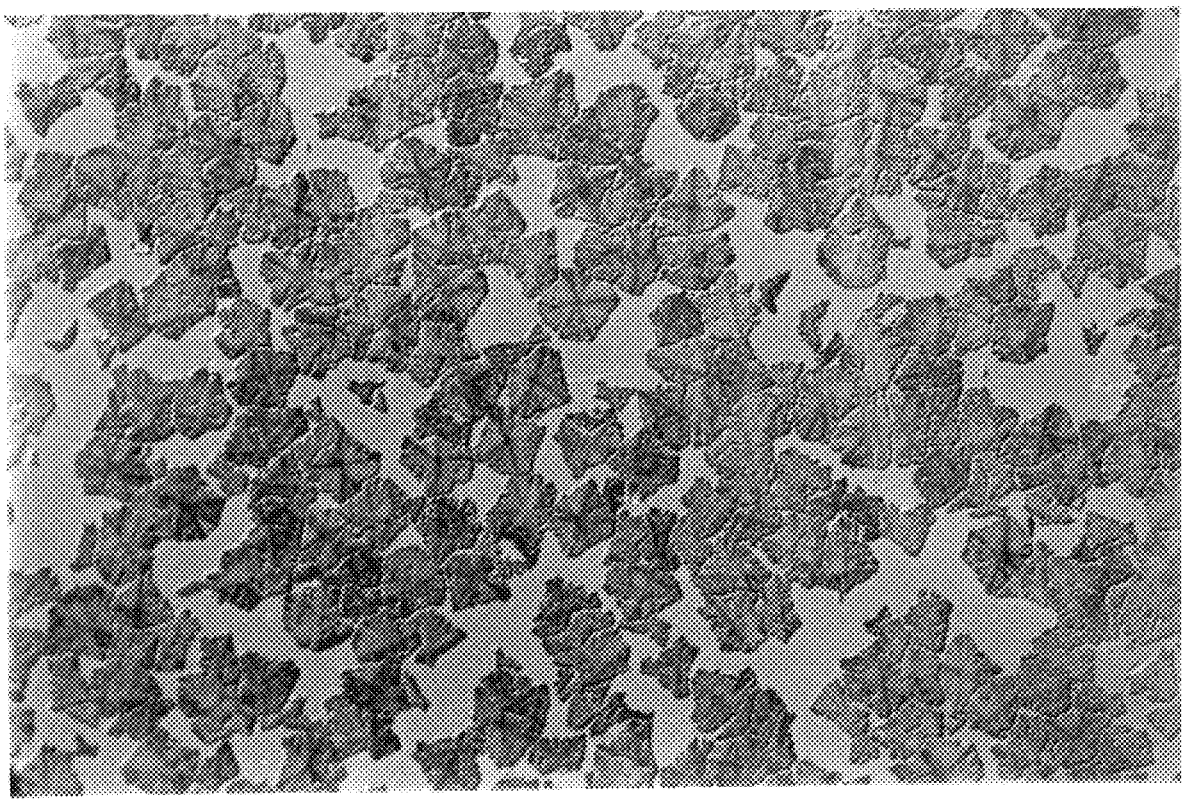

FIG. 2 shows the crystal growth rate for SSP4 and SSP6 compositions. It is observed that $P_2O_5$ has the same effect on growth and nucleation kinetics, i.e., increasing amounts of $P_2O_5$ decrease the growth rate. The ability to control the nucleations and growth rates for this material results in the ability to control the final mechanical properties of the glass/ceramic.

III. Glass and Glass-Ceramic Bioactivity

A bioactive material undergoes chemical reactions at the interface between tissues and the implant material. The surface reactions lead to bonding of tissues at the interface.

A common characteristic of all bioactive implants is formation of a hydroxy-carbonate apatite (HCA) layer on their surface when implanted.

One of the most versatile surface analysis techniques to analyze changes in glass surface chemistry is Fourier Transform Infrared Spectroscopy (FTIRS). The FTIR method gives information about the chemical composition, such as Si—O—Si and P—O vibrational modes, of the surface and it can also detect phase changes occurring within a surface layer. For example, the crystallization of a hydroxy-carbonate apatite layer on a bioactive glass surface is easily detected by FTIRS. The molecular vibrations in the region of special interest for bioactive glasses are listed in table 2.

TABLE 2

Infrared frequencies for functional groups on a bioactive glass surface.

| Wavenumber (cm$^{-1}$) | Vibrational Mode | |
|---|---|---|
| 1350–1080 | P=O | stretch |
| 1250–1100 | P=O | assoc. |
| 940–860 | Si—O—Si | stretch |
| 890–800 | C-0 | stretch |
| 1175–710 | Si—O—Si | tetrahedra |
| 610–600 | P-0 | bend crystal |
| 560–550 | P-0 | bend amorph. |
| 530–515 | P-0 | bend crystal |
| 540–415 | Si—O—Si | bend |

III. Thermal Treatment

The nucleation and crystallization studies described previously were used to prepare different volume fractions of crystals for SS, SSP4 and SSP6 glass compositions. Table 3 shows the thermal treatment range used for the three compositions.

TABLE 3

| | Thermal treatments | | | |
|---|---|---|---|---|
| Composition | TNUCL. (° C.) | tNUCL. (hrs) | TGROWTH (° C.) | tGROWTH (min) |
| SS | 550 | 0–3 | 620–640 | 6–22 |
| SSP4 | 550 | 1–25 | 650 | 38 |
| SSP6 | 550 | 150 | 680 | 13–66 |

FIG. 3 presents the optical microstructures of glass-ceramics for several volume percentages of crystallization (8, 36, 60, 87 and 100%) for the SSP6 composition. The microstructures obtained by homogeneous nucleation of, SSP6, glasses are very uniform, grain sizes range from 8 to 25 $\mu$m. This uniform microstructure results in a more even distribution of forces when the glass/ceramic is under physiological load.

B. Solution Test

In vitro testing of bioactive glasses use different types of solutions to reproduce physiological body fluid. The closest solution to human plasma is Simulated Body Fluid (SBF-K9) which was used for our experiments.

C. Bioactivity Tests

The in vitro bioactivity tests were conducted in with the ratio of glass or glass-ceramic surface area (SA) to solution volume (V) fixed at 0.1 cm$^{-1}$ and the temperature set at 36.5° C. The solutions were stirred by a magnetic stirring bar. FTIR spectroscopy was performed on all samples before and after exposure to SBF-K9 solution.

Figure 4:
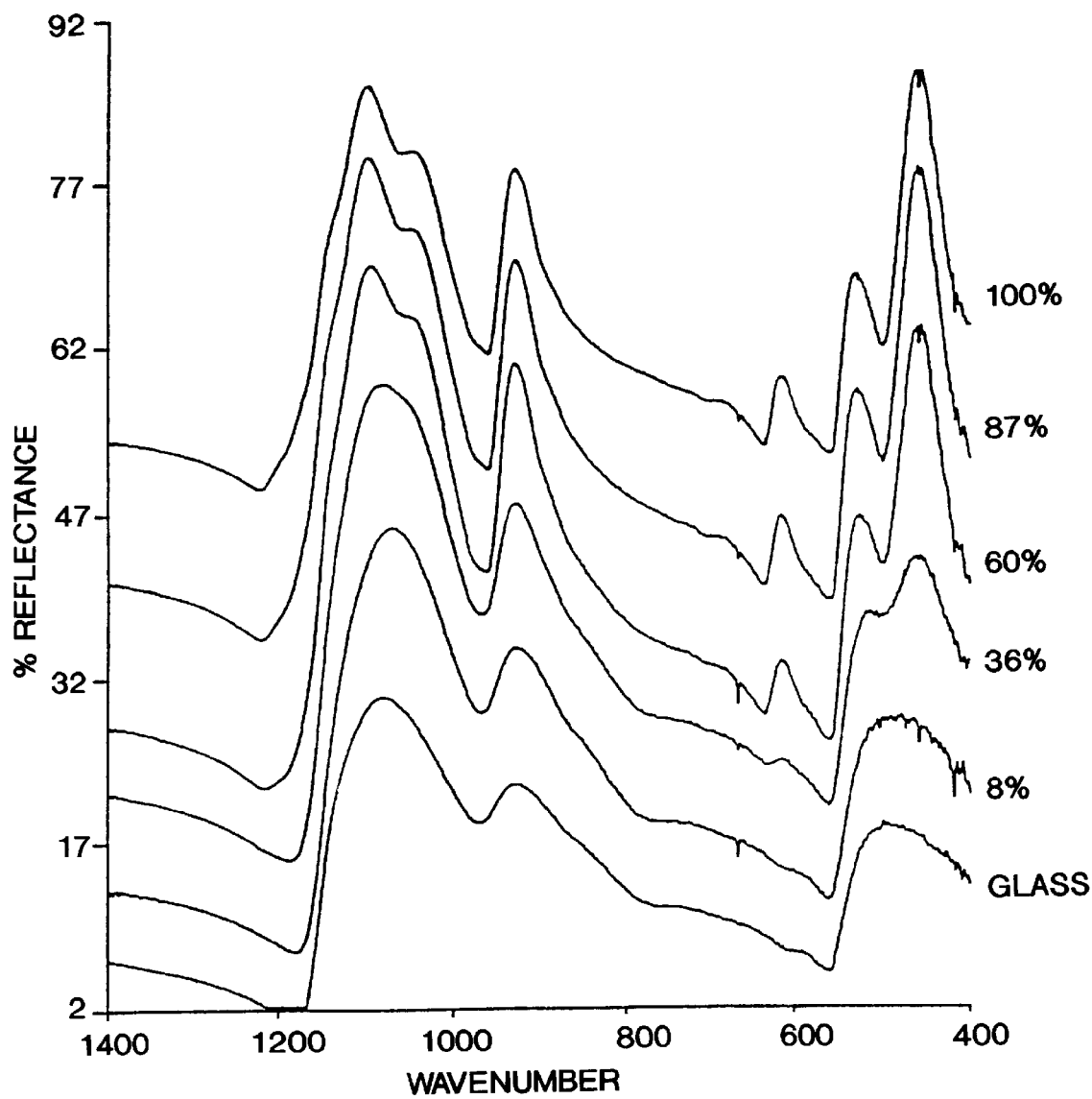
FIGS. 4, 5, and 6 show FTIR spectra of the SSP6 glass and glass-ceramics before exposure to SBF and after 20 and 40 hours.
Figure 5:
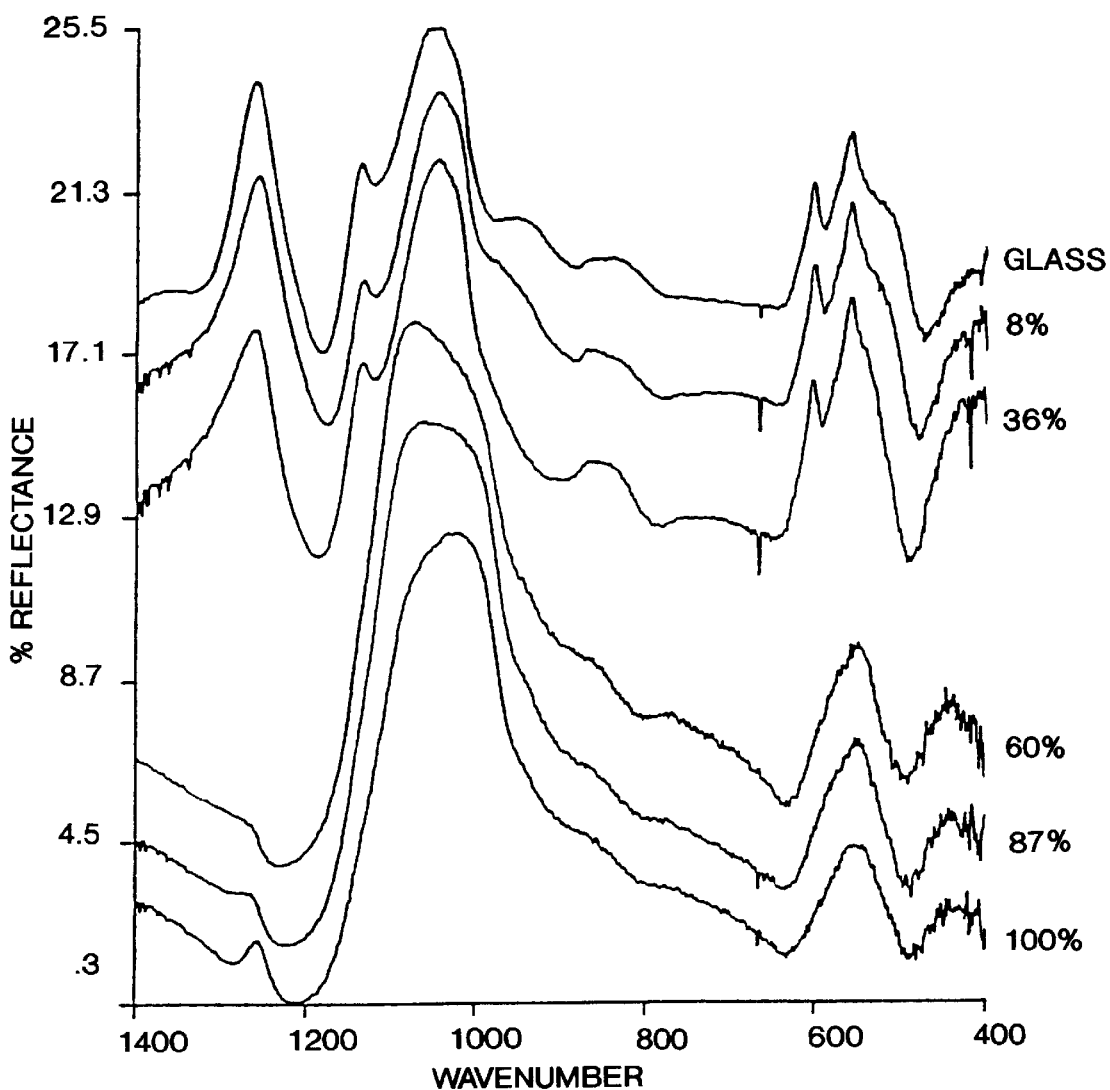
Figure 6:
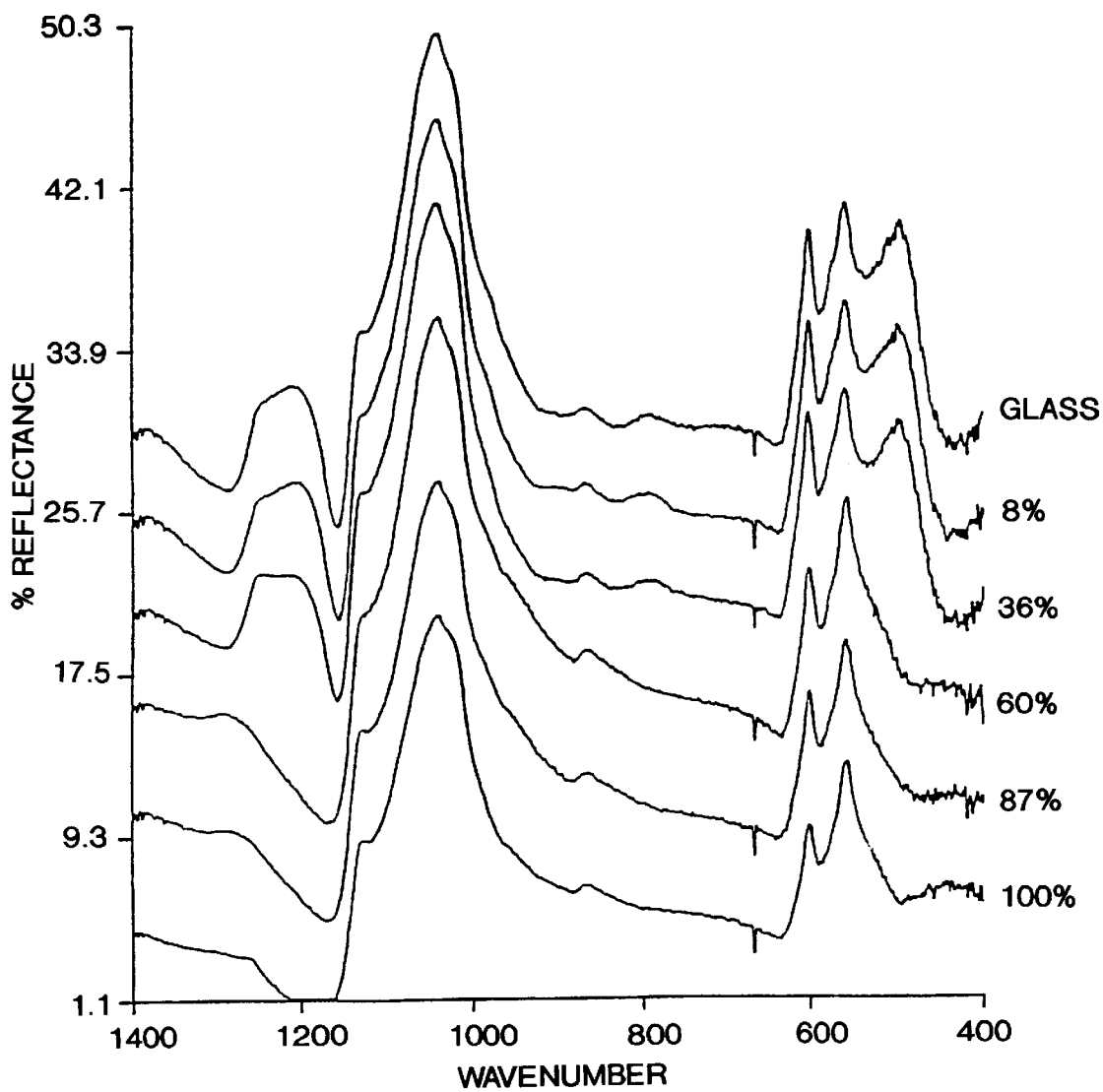

FTIR spectra of the SSP6 glass and glass-ceramics before exposure to SBF and after 20 and 40 hours are shown in FIGS. 4, 5 and 6. The most noticeable changes in the IR spectra in FIG. 4, relative to the unreacted amorphous glass, are seen between 700 cm$^{-1}$ and 400 cm$^{-1}$. Above 36 volume percent crystallization several new peaks emerge at 460 cm$^{-1}$, 575 cm$^{-1}$ and 650 cm$^{-1}$ which are attributed to the develop crystalline HCA phase. When specimens are exposed to SBF solution for 20 hours, FIG. 5, the glass-ceramics with more than 60% crystallinity show only amorphous calcium phosphate film development. However, glass-ceramics below 60% crystallinity show crystalline HCA formation at the same time period. After 40 hours exposure to SBF, FIG. 6, the glass ceramics above 60% crystallinity also exhibited fully developed crystalline HCA layers. In both FIGS. 5 and 6 there is an absence of most peaks associated with the crystalline phase of the glass-ceramic, all peaks shown are due to either the amorphous calcium phosphate layer or crystalline phases of HCA indicating a well developed HCA layer which masks the underlying glass/ceramic surface.

The rate of formation of a crystalline HCA layer is a very important characteristic of a bioactive material. Nevertheless, the level of the bioactivity can determine the interface thickness and the soft tissue bonding (Bioactivity Index, $I_B>8$).

Figure 7:
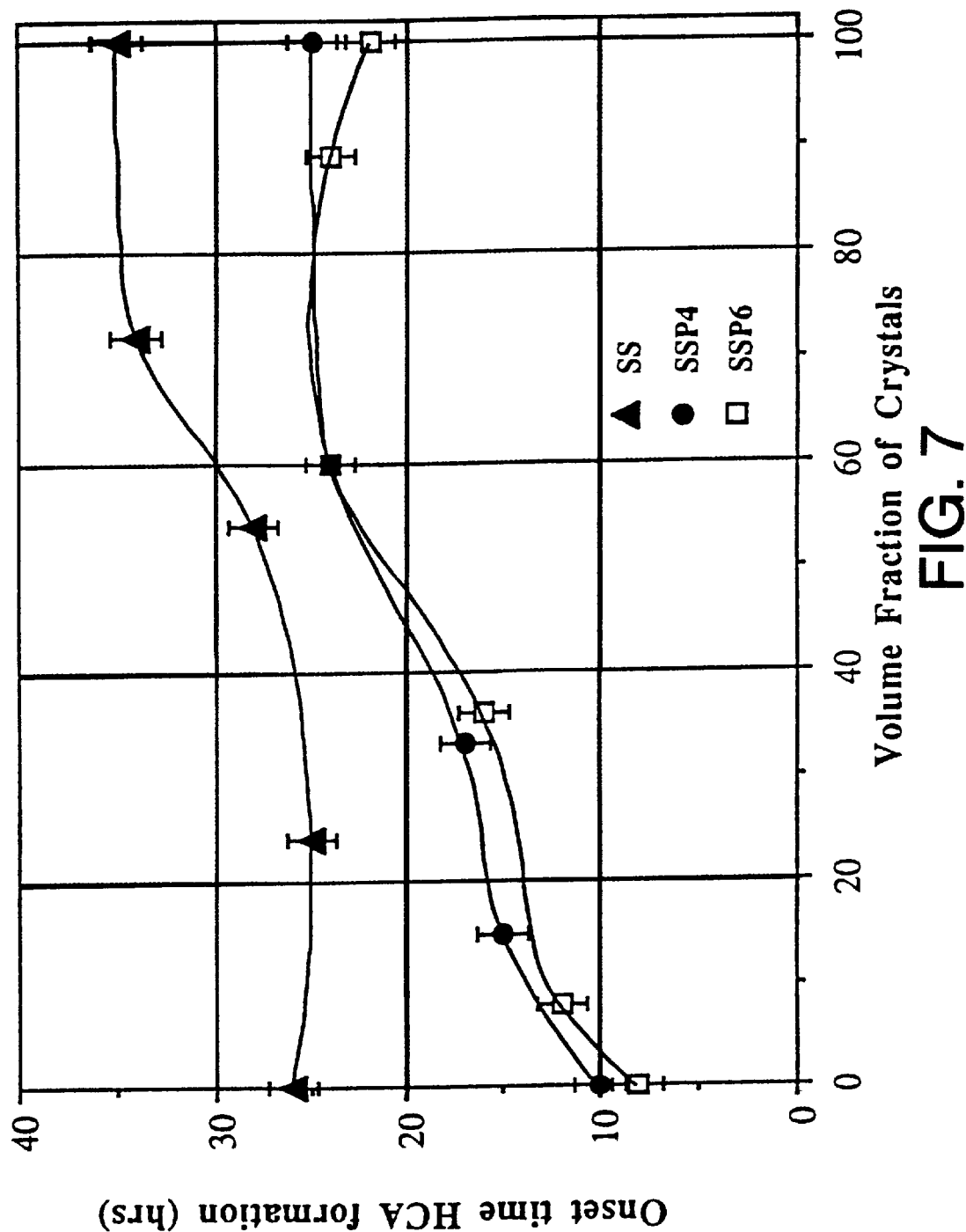
FIG. 7 shows the bioactivity levels of SS, SSP4 and SSP6 glass and glass-ceramics disks which were exposed to SBF solution between 7 and 96 hours to measure the onset time for HCA layer formation.
Figure 8A:
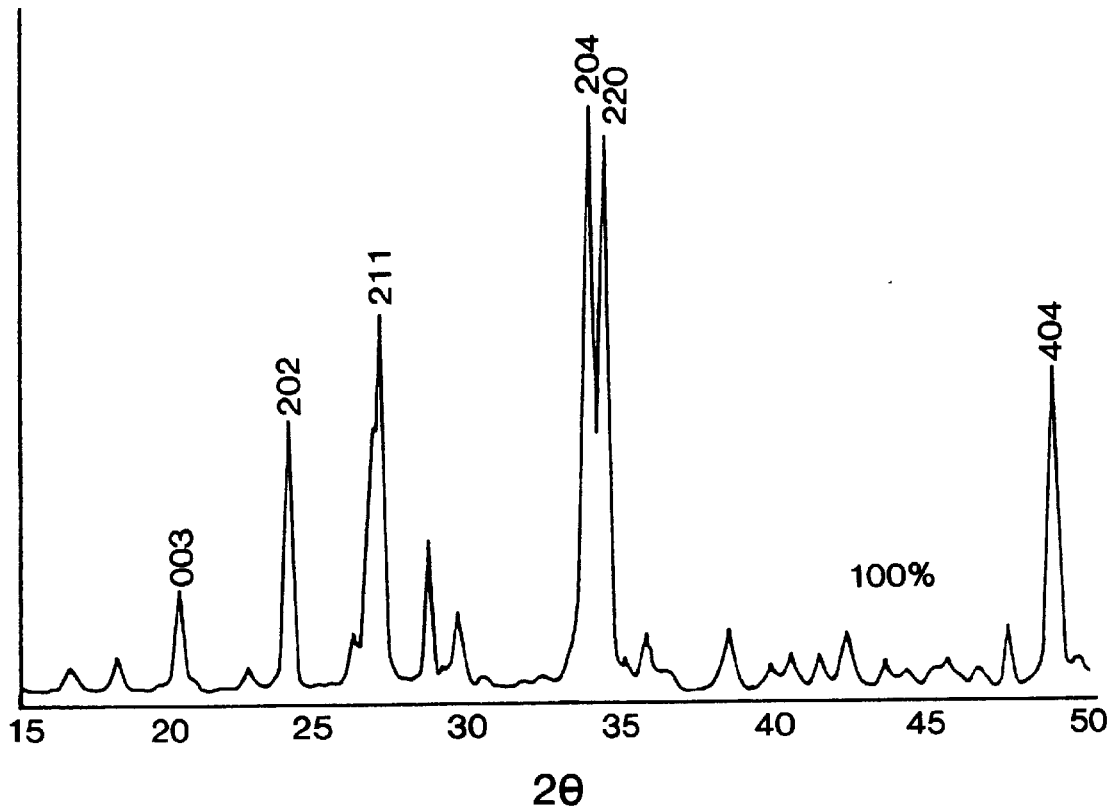
FIG. 8 shows the x-ray diffraction results of different volume fractions of crystals for the SSP4 composition.
Figure 8B:
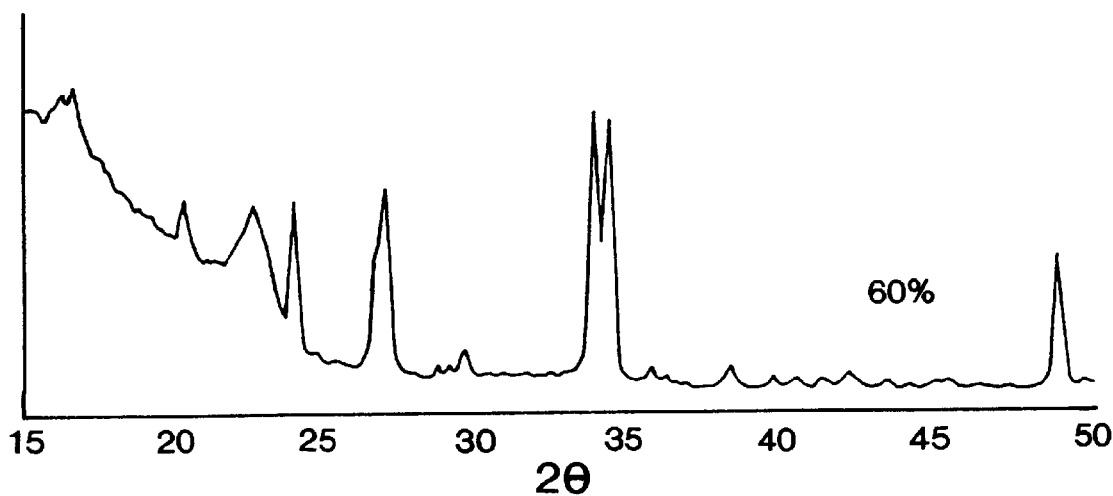
Figure 8C:
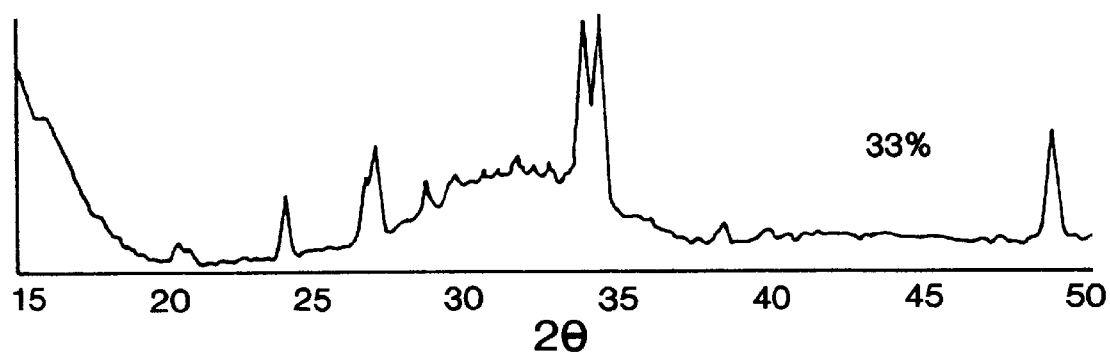
Figure 8D:
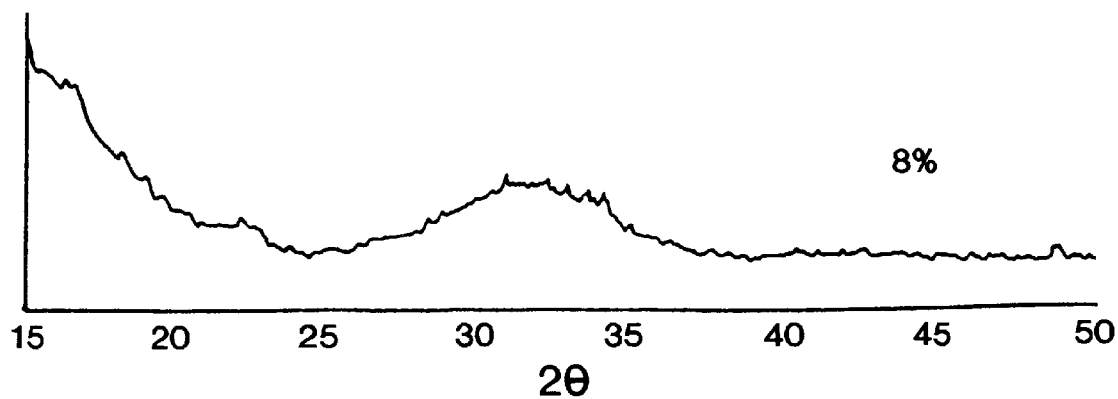

The onset time for HCA formation is used to evaluate the bioactivity level. SS, SSP4 and SSP6 glass and glass-ceramics disks were exposed to SBF solution between 7 and 96 hours to measure the onset time for HCA layer formation The results are shown in FIG. 7. These curves demonstrate the ability to control the bioactivity of the glass/ceramic by controlling the microstructure.

Most commercial bioactive glass-ceramics previously developed have lower bioactivity levels. For example, A/W glass-ceramics develop the HCA layer after 7 days exposure in SBF solution (12 times slower than 45S5).

All of the glass and glass-ceramics studied formed a crystalline HCA layer when exposed to SBF solution. For composition SSP6 the onset time of HCA crystallization was shifted from 10 hrs for the amorphous glass to 22 hrs for the 100% crystalline material. Almost the same behavior was shown by the SSP4 composition, from 10 hrs to 25 hrs. For both compositions the onset time of HCA formation increased with percentage crystallinity until 60% crystallinity was reached, at which point the onset time remained relatively constant. The composition without $P_2O_5$, SS, showed a different behavior; e.g., the percentage of crystallinity did not affect the bioactivity level (27 hrs to develop the onset time for a HCA crystalline layer) until 60% crystallinity was present. Above 60% crystallinity the time for HCA formation increased from 27 hrs for 35 hrs to 100% crystallized samples.

The in vitro test results show that SS, SSP4 and SSP6 glass and glass-ceramics maintain a high bioactivity level when tested in SBF solution. There was no substantial loss in bioactivity with crystallinity, even up to 100%. The reaction rates for formation of HCA observed for the SSP4 and SSP6 glass-ceramics were up to seven times faster than reported for other bioactive glass-ceramics, especially A/W glass-ceramic.

IV. Mechanical Properties

The mechanical properties of glass-ceramics, among others variables, depend on volume fraction, grain size, crystal phase and shape of crystals. The effect of amount of crystals and grain size on mechanical properties was also studied. The size distribution of crystals of all glass-ceramics produced in this system was always very uniform, as shown by optical microscopy. In all compositions studied, x ray diffraction revealed only one crystalline phase, $1Na_2O.2Ca0.3SiO_2$ (FIG. 8). FIG. 8 shows the x ray diffraction results of different volume fractions of crystals for the SSP4 composition.

The effects of crystallization on the following mechanical properties were determined: fracture strength, elastic modulus, microhardness and fracture toughness. All mechanical properties were improved by crystallization. The partially crystallized glass-ceramics are much stronger and tougher than the amorphous glass, while still in the range of mechanical properties of natural bone.

A. Effect of Volume Fraction of Crystals

1. Thermal Treatment

To evaluate the effect of the amount or volume fraction of crystals on glass-ceramics the grain size must be fixed. To accomplish this the thermal treatment must be determined for each kind of microstructure. The second step of the heat treatment, growth, must be the same for every microstructure to produce the same grain size. The nucleation treatment is used to change the volume fraction of crystal desired.

Figure 9A:
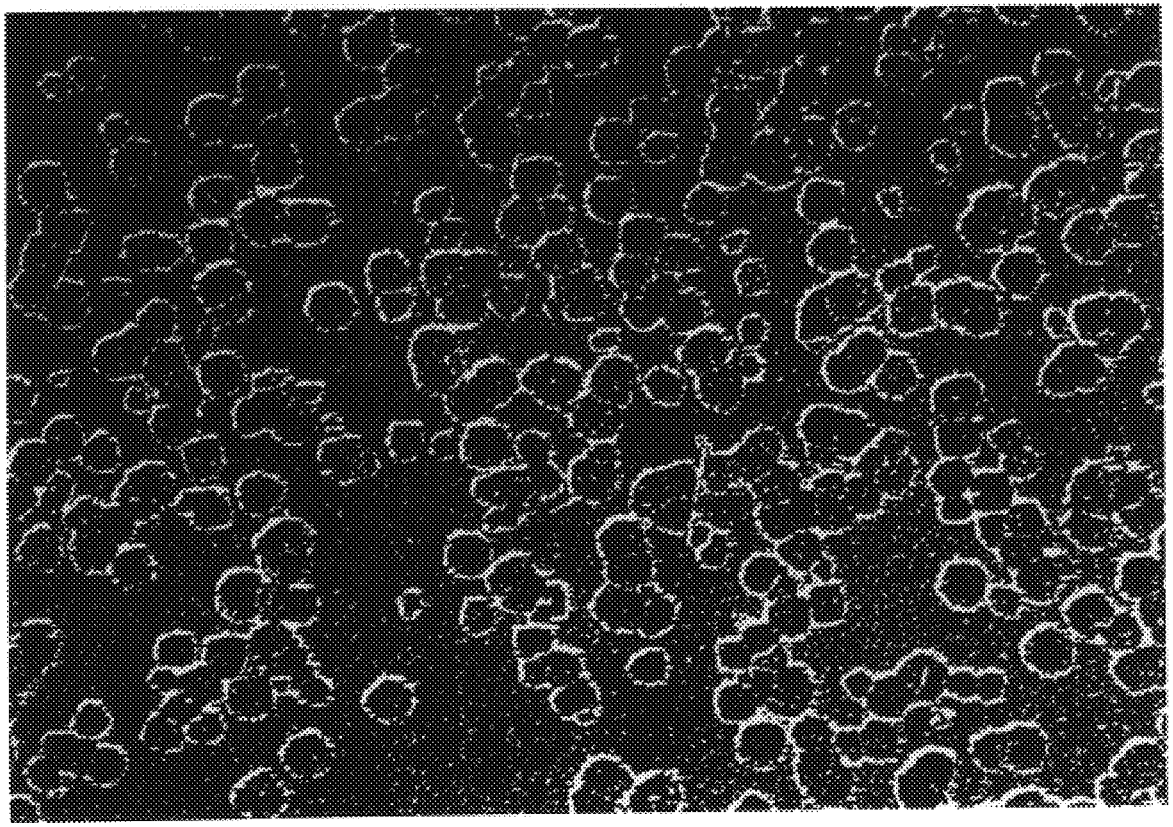
FIG. 9 show respective glass-ceramics microstructures.
Figure 9B:
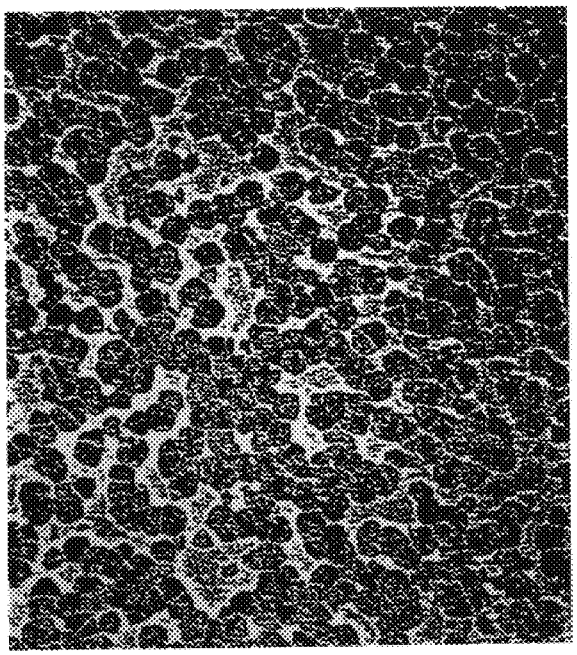
Figure 9C:
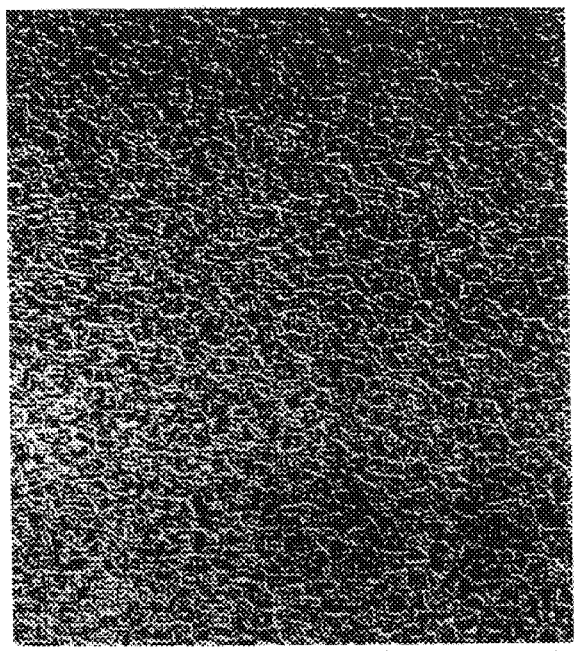

For the SSP4 composition we produced three different percentages of crystals (34, 60 and 100%) all with 13 $\mu$m grain size. The heat treatments used are shown in Table 4. FIG. 9 show the respective glass-ceramics microstructures.

TABLE 4

SSP4 thermal treatments to produce 13 $\mu$m grain size.

| Percent Crystallinity (%) | T nucleation (° C.) | t nucleation (hrs) | T growth (° C.) | t growth (min) |
|---|---|---|---|---|
| 34 | 550 | 3.2 | 650 | 38 |
| 60 | 550 | 6 | 650 | 38 |
| 100 | 550 | 25 | 650 | 38 |

2. Modulus of Rupture (MOR)

The strength of a material is the level of stress at which it fractures. Since materials break at different stress levels under compression loads than under either stretching (tensile) loads or bending loads (modulus of rupture, MOR, or flexural strength), it is necessary to specify the testing procedure used. To measure the MOR of glass-ceramics a four point load or bend test is preferred. The modulus of rupture of rectangular specimens is given by equation 2.

$$MOR=3P(L-a)/2bd^2 \qquad (2)$$

where P is the load required to break the specimen, L is the distance between the outer supports, a is the distance between the inner two load application points, b is the width of the specimen and d is the depth of the specimen.

The most important parameters to control in MOR determinations are the rate of loading, the ratio of span-to-specimen thickness (L/d), and the specimen alignment. The ratio L/d must be at least 10 to 1 or corrections to equation 2 must be made. The specimen cannot twist while being loaded.

In all modulus of rupture determinations the following conditions were used in this experiment: rate loading 0.1 mm/min and ratio L/d=8. The specimens were rectangular with width 5.4 mm and 3.5 mm depth.

Figure 10:
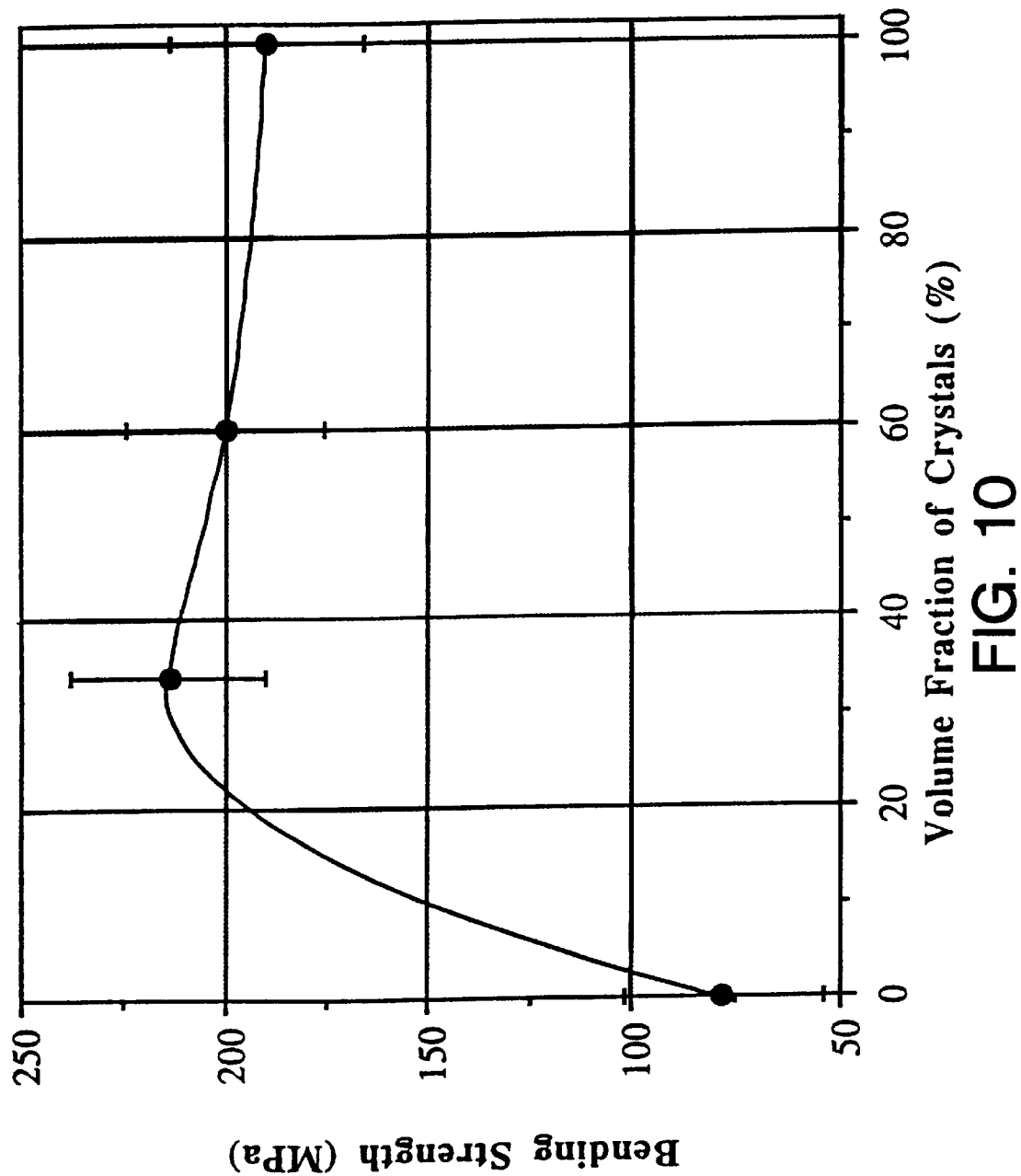
FIG. 10 shows the MOR (Modulus of Rupture) for the SSP4 composition as a function of the volume fraction of crystals with a constant grain size of 13μm.

FIG. 10 shows the MOR for the SSP4 composition as a function of the volume fraction of crystals with a constant grain size of 13 $\mu$m. Each point corresponds to the average at least of 6 samples with the error bars indicating the standard deviation. The flexural strength increased 2.7 times, from 80 MPa glass to 214 MPa for the glass-ceramic with 34% volume fraction of crystals. Glass-ceramics with greater then 34% crystallization show a slight decrease in MOR but the values are still much higher than the glass. There is no statistical difference between the MOR of samples with various percentages of crystals, as determined by students t-test.

3. Modulus of Elasticity

One of the most important physical properties of load bearing implants is the Modulus of Elasticity, i.e., the stiffness of the material. When the implant has a much higher modulus of elasticity than bone a stress shielding problem occurs. The interface between a stress shielding bone and an implant deteriorates as the bone is weakened. Loosening and or fracture of bone, the interface, or the implant will result.

Figure 11:
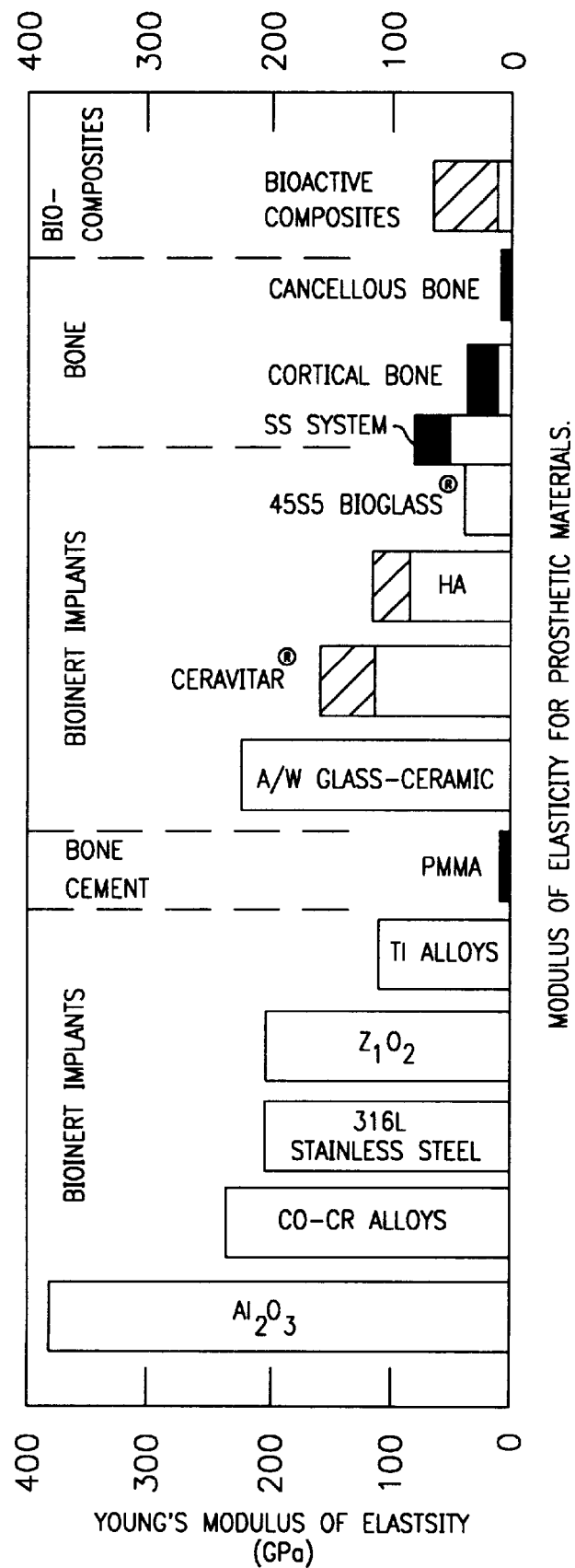
FIG. 11 show the Modulus of Elasticity for different implant materials and of cortical and trabecular bone.

FIG. 11 show the Modulus of Elasticity for different implant materials and of cortical and trabecular bone. The Modulus of Elasticity of cortical bone ranges between 7 to 25 GPa while cancellous goes from 0.05 to 0.5 Gpa. The modulus of elasticity for the present examplary ceramics is in the range of cortical bone.

Modulus of Elasticity can be measured using the load versus deflection curve obtained during four point bending test. It is calculated by equation 3;

$$E = P \cdot (L_1 - L_2) \cdot (2L_1^2 + 2L_1L_2 - L_2^2)/96 \cdot I \cdot \delta$$

(3) where P is the load, $L_1$ is the distance between the outer support peas, $L_2$ is the distance between the inner loading peas, $\delta$ is deflection and I is the geometric moment of inertia ($I = bd^3/12$ for a rectangular beam of width b and height d).

Figure 12:
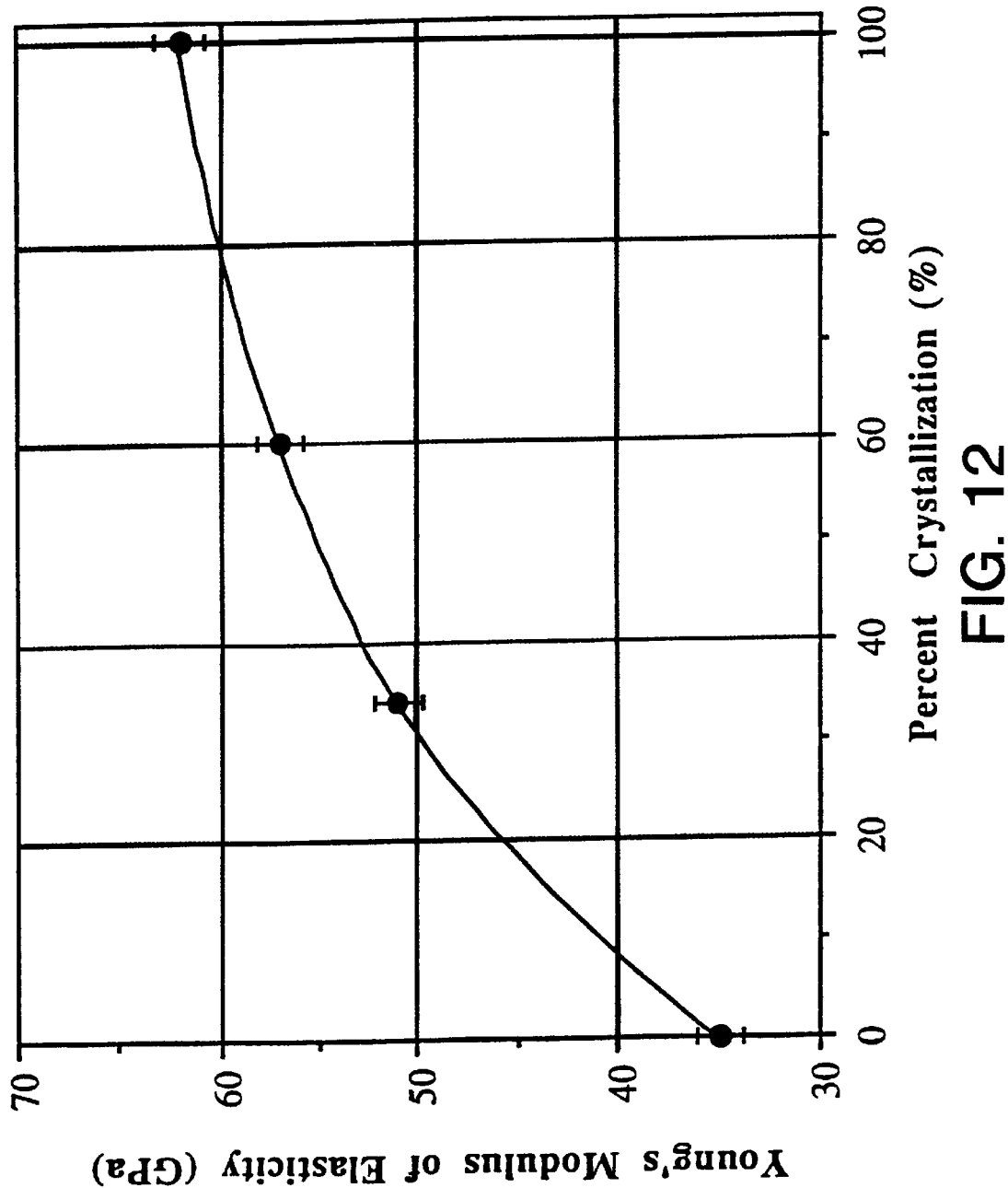
FIG. 12 shows the modulus of elasticity for the SSP4 composition as a function of the volume fraction of crystals for 13 μm grain size.

FIG. 12 shows the modulus of elasticity for the SSP4 composition as a function of the volume fraction of crystals for 13 μm grain size. The modulus increases with crystallization from 35 GPa for the glass to 62 GPa when totally crystallized, 77% higher than glass. In spite of the modulus increase with crystallinity for the SS system, it is still a good match with the modulus of cortical bone when compared with the other crystalline bioactive materials. It is very important to observe that the modulus of elasticity can be controlled by varying the percentage of crystallinity. This results in values between 50 and 62 GPa without decreasing mechanical strength and bioactivity (FIGS. 9 and 7). Note that modulus of elasticity in this range increases almost linearly with the percentage of crystallinity. This linearity allows good control of microstructures and resultant mechanical properties.

4. Vickers Microhardness

Vickers microhardness measurements in a multiphase system must be made in all phases to evaluate the results. As mentioned previously, in the system SS we have only one crystalline phase, so microhardness measurements were made inside both the glass and the crystal phase. SSP4 and SSP6 glass-ceramic samples were prepared with different percentages of crystallinity and tested. The thermal treatment for the SSP4 composition with 13 μm grain size is given in table 5.

TABLE 5

Thermal Treatment SSP4, 13 pm grain size, for microhardness test.

| Percent Crystallinity | T nucleation (° C.) | t nucleation (hrs) | T growth (° C.) | t growth (min) |
|---|---|---|---|---|
| 15 | 550 | 1.2 | 650 | 38 |
| 33 | 550 | 3.1 | 650 | 38 |
| 62 | 550 | 6.2 | 650 | 38 |
| 89 | 550 | 11 | 650 | 38 |
| 100 | 550 | 25 | 650 | 38 |

Figure 13:
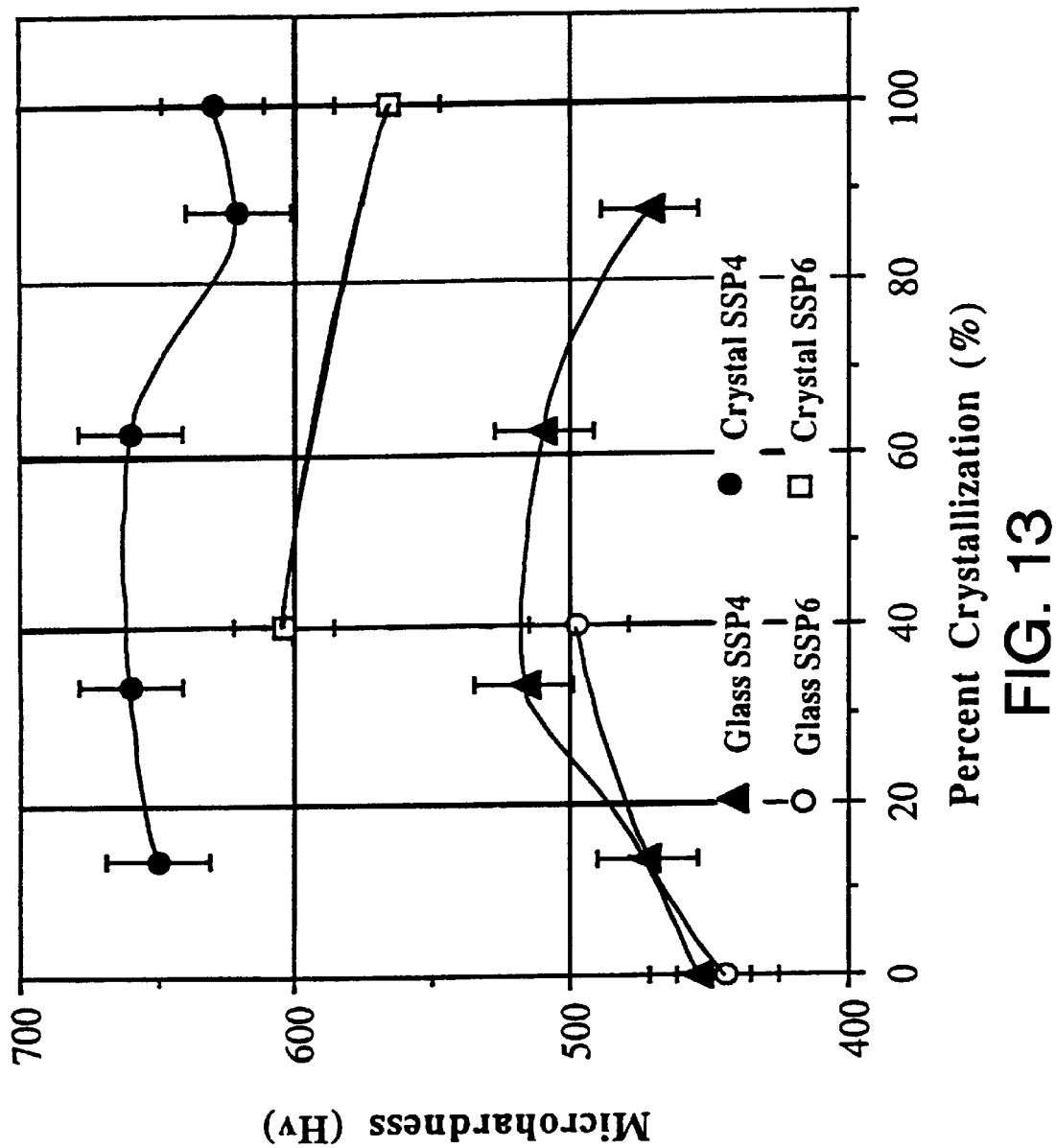
FIG. 13 show the Vicker Hardness of the SSP4 and SSP6 glass and glass ceramic as a function of percent crystallization.

FIG. 13 show the microhardness results, where each point represents the average of at least 10 measurements. It is observed that the crystals are harder than the glass phase and increase from 44 to 28% for SSP4 and about 22% for SSP6. Crystals in SSP4 composition are harder than SSP6.

The microhardness in glass phase increases with the percent crystallization until about 40% and between 40 and 60% is almost invariable and decreases when the crystallization is greater than 60%. The microhardness in the crystal phase is almost constant until a volume fraction of 62% and decreases with a higher percentage of crystallization. This behavior is observed in both compositions, SSP4 and SSP6, and can be due to microstresses between the crystal and glass phase.

Residual microstresses anise in the partially crystallized glass-ceramics below the glass transition temperature during cooling due to the thermal expansion coefficient difference between the glass and crystal phase. Microstress levels are dependent on the elastic properties, glass and crystal, and the crystal planes.

The residual microstresses were measured using x ray diffraction and showed that they reach 140 MPa at the interface between glass and crystals. Theoretically, microstresses decrease when the crystals come near and impinge each other. At this point the residual microstresses start to decrease so, microhardness decreases in glass-ceramics with a high percent of crystallization.

4. Fracture Toughness

Glass and glass-ceramic fracture toughness was measured by the indentation method using a standard microhardness instrument to press a hard indentor into the surface of the solid. When a pyramid indentor is forced into a glass or glass-ceramic specimen it produces a plastic impression, a system of cracks that run along the boundary of the impression at the loading stage, and a system of radial cracks that form after load removal under the action of residual tensile stresses, FIG. 14. The magnitude and distribution of these stresses and, correspondingly, the character and size of the resultant cracks depend on both the indentor geometry and the hardness, elastic constants, relaxability, and other properties of the materials as described in equations 4 and 5.

$$K_{1c} = 0.24 \alpha^{-1} (E/H)^{0.4} (P/c^{3/2})(c/a)^{c/(18a)} \quad (4)$$

where $$\alpha = 14\{1 - 8[(4v - 0.5)/(1+v)]^4\} \quad (5)$$

E is Modulus of Elasticity, H is the hardness, P is the load applied to the indentor, c is the crack length as measured from the center of the impression, a is the size of indentation and v is Poisson's ratio.

Figure 14:
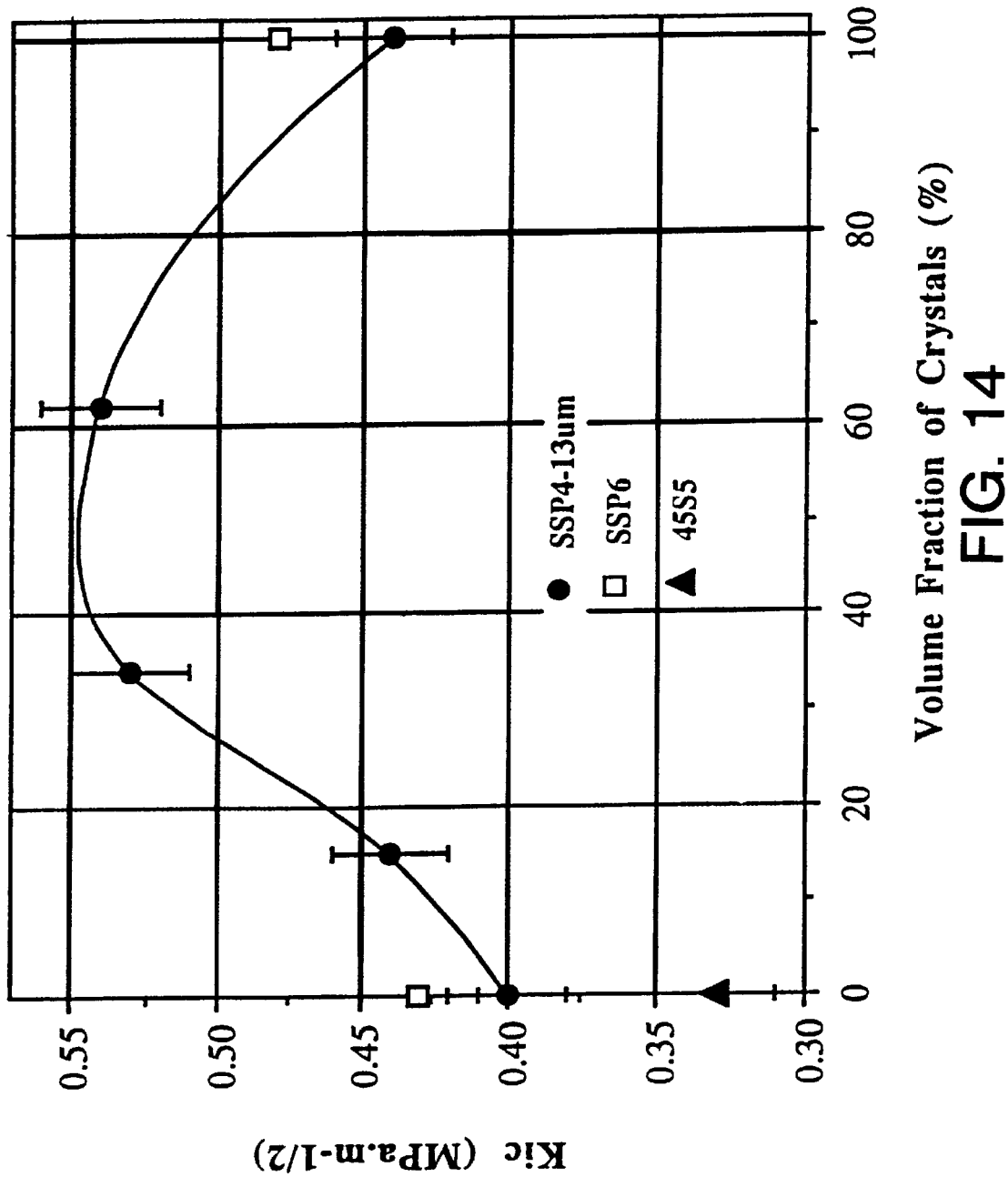
FIG. 14 shows the fracture toughness ($K_{ic}$) of the SSP4 (13 μm grain size).

The glass and glass-ceramic specimens were prepared with the same thermal treatment shown in table 5, cut and polished to a 1 μm surface finish. It is observed that the fracture toughness increases with percentage of crystallization until 34%. Within the range from 34 to 62% of crystallization $K_{1c}$ is almost constant, $K_{1c}$ decreases for volume fractions of crystal greater than 62% (FIG. 14).

The best fracture toughness is into the region with 34 to 62% of crystallinity and it is 35% higher than the amorphous glass. The SSP6 composition shows somewhat higher fracture toughness than SSP4 on two points, glass and glass-ceramic totally crystallized, where measurements were made.

B. Effect of Grain Size

As shown previously, crystallization improves modulus of rupture, hardness, fracture toughness and modulus of elasticity. The microstructure that shows the best mechanical proprieties ranges from 34 to 60% of crystallization and 13 μm grain size. To evaluate the grain size effect, modulus of rupture versus microstructure of samples with varying grain size from 5 to 21 μm at two volume fractions of crystallization (34 and 60%) was measured.

1. Thermal Treatment

Thermal treatment schedules were developed to produce specimens with constant volume fraction of crystallization but different grain sizes. The nucleation and growth treatments used are given in table 8. Figure Crystal microstructures showed a very uniform distribution of crystals for each thermal treatment.

2. Modulus of Rupture

Four point bending modulus of rupture tests were made in the same conditions described previously, section IV.A.2.

All partially crystallized glass-ceramics are stronger than the amorphous glass, by at least 2.2 times. Glass-ceramics that are partially crystallized with 34% of crystallization have better modulus of rupture than the glass-ceramics with 60% crystals. The same behavior was observed in FIG. 10.

Theoretically, the modulus of rupture should increase with smaller grain sizes. This was observed for grain sizes from 21 to 13 $\mu$m. However, there was no improvement with grain sizes smaller than 13 $\mu$m. The worst result is 5 $\mu$m grain size and 60% of crystallization.

The preferred material for clinical implants is a glass-ceramic partially crystallized with 13 $\mu$m grain size and 34% of crystallization. This material has optimal mechanical performance and shows HCA formation after only 17 hours, in vitro testing.

TABLE 6

Thermal Treatment Schedules, SSP4 composition, 34 and 60% of crystallization.

| Percentage of Crystallinity | T nucleation (° C.) | t nucleation (hrs) | T growth (° C.) | t growth (min) | Grain Size ($\mu$m) |
|---|---|---|---|---|---|
| 34 | 550 | 42 | 650 | 14 | 5 |
| 60 | 550 | 100 | 650 | 14 | 5 |
| 34 | 550 | 8 | 650 | 26 | 9 |
| 60 | 550 | 16 | 650 | 26 | 9 |
| 34 | 550 | 3.2 | 650 | 38 | 13 |
| 60 | 550 | 6 | 650 | 38 | 13 |
| 34 | 550 | 1 | 650 | 62 | 21 |
| 60 | 550 | 1.9 | 650 | 62 | 21 |

Other Example:

Another comparative example is A/W glass ceramic. A/W is made from a parent glass in the system $3CaO.P_2O_5$—$CaO$—$SiO_2$—$MgO.CaO.2SiO_2.CaF_2$ prepared by conventional melt-quenching. The parent glass is then crystallized at 1050° C. at a rate of 5° C./minute. This method results in bulk glass with many cracks and no structural integrity due to a change in volume of the crystalline phase vs. the original glass phase. The bulk glass is then crushed into 5 micron powder and hot pressed into a solid shape and refired at 830° C. to full densification. The resultant glass ceramic can then be machined into the desired shape.

Glass/ceramic compositions of the present invention can be made by casting the parent glass into graphite molds to near net shape parts. The parts are then nucleated and crystallized without a volume change resulting in crack free bulk glass/ceramic with structural integrity. A/W glass has a modulus of elasticity much higher than that of the glass ceramic or bone of the present invention. A mismatch between the implant material and the host bone can result in stress shielding and resorption of the host bone. In comparison, the glass/ceramic of the present invention can be tailored to match the mechanical properties of the host bone (see FIG. 11) reducing the problems associated with stress shielding.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A bioactive ceramic composition comprising by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 volume percent and a crystalline phase $1Na_2O.2CaO.3SiO_2$.

2. The bioactive ceramic composition of claim 1, having a grain size of about 13 $\mu$m.

3. The bioactive ceramic composition of claim 1, having a flexural strength of 100 MPa to 214 Mpa.

4. The bioactive ceramic composition of claim 1, having a modulus of elasticity of between 7 to 25 Gpa.

5. The bioactive ceramic composition of claim 1, having a fracture toughness of between 0.40 and 0.55 $K_{ic}$.

6. A process for making the bioactive ceramic composition of claim 1, comprising nucleation heating a bioactive glass to form nucleates and thereafter crystal growth heating said nucleates to grow crystals.

7. The process of claim 6, wherein said nucleation heating is conducted at about 550° C.

8. The process of claim 6, wherein said nucleation heating is conducted for 1–25 hours.

9. The process of claim 6, wherein said crystal growth heating is conducted at a temperature of 620–680° C.

10. The process of claim 6, wherein said crystal growth heating is conducted between 6 and 66 hours.

11. An implant comprising a bioactive ceramic composition of by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 volume percent and a crystalline phase $1Na_2O.2CaO.3SiO_2$.

12. An orthopedic load bearing implant comprising a bioactive ceramic composition of by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 volume percent and a crystalline phase $1Na_2O.2CaO.3SiO_2$.

13. A dental load bearing implant comprising a bioactive ceramic composition of by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 volume percent and a crystalline phase $1Na_2O.2CaO.3SiO_2$.

14. A biocompatable polymer comprising a polymer and a bioactive ceramic composition of by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 percent and a crystalline phase $1Na_2O.2CaO.3SiO_2$.

15. A reinforcement fiber comprising a bioactive ceramic composition of by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 volume percent and a crystalline phase $1Na_2O.2CaO.3SiO_2$.

16. A reinforcement particulate comprising a bioactive ceramic composition of by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 volume percent and a crystalline phase $1Na_2O.2Ca0.3SiO_2$.

17. An injectable mixture for soft tissue treatment comprising a bioactive ceramic composition of by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 volume percent and a crystalline phase $1Na_2O.2Ca0.3SiO_2$.

18. A method for treating orthopedic conditions comprising, contacting a patient in need of such treatment with an effective regenerating amount of a bioactive ceramic composition of by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 volume percent and a crystalline phase $1Na_2O.2Ca0.3SiO_2$.

19. Autogenous bone chips comprising a bioactive ceramic composition of by weight percent 47 to 51% $SiO_2$, 23 to 25% CaO, 23 to 25% $Na_2O$ and 0 to 6% $P_2O_5$, the bioactive ceramic having a bioactivity level such that the composition forms at least a thin layer of HCA within about 30 hours of implantation into a patient, the composition having a crystallinity of 34 to 60 volume percent and a crystalline phase $1Na_2O.2Ca0.3SiO_2$.

* * * * *